United States Patent [19]

Chatterjee et al.

[11] Patent Number: 5,118,707

[45] Date of Patent: Jun. 2, 1992

[54] COMPOSITIONS FOR REGULATING SKIN WRINKLES COMPRISING A BENZOFURAN DERIVATIVE

[75] Inventors: Ranjit Chatterjee, Cincinnati; Rajesh Kapoor, Fairfield, both of Ohio

[73] Assignee: The Procter & Gamble Company, Cincinnati, Ohio

[21] Appl. No.: 674,628

[22] Filed: Mar. 25, 1991

Related U.S. Application Data

[63] Continuation-in-part of Ser. No. 606,295, Oct. 31, 1990, abandoned.

[51] Int. Cl.$^5$ .............................. A61K 31/34
[52] U.S. Cl. .................................. 514/469
[58] Field of Search ........................ 514/469

[56] References Cited

U.S. PATENT DOCUMENTS

| | | | |
|---|---|---|---|
| 4,098,882 | 7/1978 | Lang/Jacquet | 424/59 |
| 4,537,903 | 8/1985 | Chang et al. | 514/456 |
| 4,704,462 | 11/1987 | Chang et al. | 549/466 |
| 4,714,711 | 12/1987 | Miller | 514/464 |
| 4,766,223 | 8/1988 | Grain et al. | 549/468 |
| 4,775,663 | 10/1988 | Forestier et al. | 514/25 |
| 4,778,805 | 10/1990 | Adams et al. | 514/320 |
| 5,039,700 | 8/1991 | Gubin et al. | 514/466 |
| 5,039,701 | 8/1991 | Schlecker et al. | 514/469 |

FOREIGN PATENT DOCUMENTS

| | | | |
|---|---|---|---|
| 165810 | 12/1985 | European Pat. Off. | 307/79 |
| 295851 | 12/1988 | European Pat. Off. | 307/86 |
| 360637 | 3/1990 | European Pat. Off. | 307/94 |

OTHER PUBLICATIONS

Heger et al., "Clinical Use and Pharmacology of Amiodarone," *Medical Clinics of North America* vol. 68, pp. 1339–1366 (1984).

"Morphological Findings in Sun Exposed and Sun Protected Skin of Patients Treated with Amiodarone", Clinical Research, vol. 36, (1988).

"Cutaneous Ultrastructural Changes and Photosensitivity Associated with Amiodarone Therapy", Journal of the American Academy of Dermatology, vol. 16, pp. 779–787, S. Waitzer, J. Butany, L. From, W. Hanna, C. Ramsay, E. Downar (1987).

"Amiodarone-Associated Pulmonary Fibrosis", Chest, vol. 92, pp. 625–630, K. Fan, R. Bell, S. Eudy & J. Fullenwider, (1987).

"Experimental Contact Photoallergenicity:Guinea Pig Models", Photodermatology, vol. 1, pp. 221–231, T. Maurer, (1984).

"Clinical Use and Pharmacology of Amiodarone", Medical Clinics of North America, vol. 68, pp. 1339–1366, J. J. Heger, E. N. Prystowsky, W. M. Milles, and D. P. Zipes, (1984).

Primary Examiner—Leonard Schenkman
Attorney, Agent, or Firm—Brahm J. Corstanje; M. B. Graff, IV; J. J. Yetter

[57] ABSTRACT

The present invnetion relates to a compositon for topical application for regulating wrinkles in mammalian skin comprising a benzofuran derivative having the structure

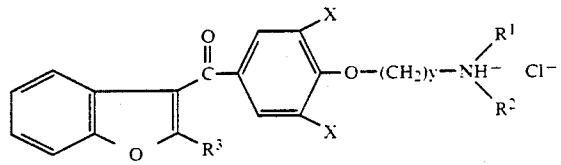

wherein $R^1$ and $R^2$ are each independently methyl or ethyl, $R^3$ is $C_1$–$C_4$ alkyl, y is an integer from 1 to about 3 and each X is independently selected from the group consisting of Cl, Br, I, F, $NO_3$, $NO_4$, $SO_3$ and $SO_4$, and a safe and effective amount of a topical carrier.

11 Claims, No Drawings

COMPOSITIONS FOR REGULATING SKIN WRINKLES COMPRISING A BENZOFURAN DERIVATIVE

This is a continuation-in-part of U.S. patent application Ser. No. 07/606,295, filed on Oct. 31, 1990, now abandoned.

TECHNICAL FIELD

The present invention relates to the field of anti-aging of skin. Specifically, the invention relates to novel compositions and methods of using the compositions for effacing and preventing wrinkles in mammalian skin.

BACKGROUND OF THE INVENTION

Skin is subject to abuse by many extrinsic (environmental) factors as well as intrinsic (aging) factors. A common extrinsic factor is exposure to ultraviolet radiation. Whether extrinsic or intrinsic, the abuse results in wrinkling of the skin. To many people, skin wrinkles are a reminder of the disappearance of youth. As a result, the elimination of wrinkles has become a booming business in youth-conscious societies. Treatments range from cosmetic creams and moisturizers to various forms of cosmetic surgery.

Amiodarone, a preferred active of the present invention, is generally known as an antiarrhythmic agent. The drug was developed in Belgium as part of a systematic approach to form a coronary vasodilator and antianginal drug. The compound is a benzofuran derivative that contains two iodine molecules, has a molecular weight of 642 daltons, and is a weak base with a pKa of 5 6. (See Waitzer, S., J. Butany, L. From, W. Hanna, C. Ramsay, E. Downar, "Cutaneous Ultrastructural Changes in Photosensitivity Associated with Amiodarone Therapy", (1987) *Journal of the American Academy of Dermatology*, Vol. 16(4), pp. 779-787.)

OBJECTS OF THE PRESENT INVENTION

It is an object of the present invention to provide a composition for topical application for regulating wrinkles in mammalian skin.

It is also an object of the present invention to provide a method of regulating skin wrinkles in mammalian skin which comprises applying to mammalian skin a topical composition.

SUMMARY OF THE INVENTION

The present invention relates to a composition for topical application for regulating wrinkles in mammalian skin comprising a benzofuran derivative having the structure

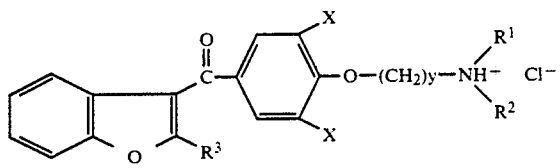

wherein $R^1$ and $R^2$ are each independently methyl or ethyl, $R^3$ is a $C_1$-$C_4$ alkyl, y is an integer from 1 to about 3 and each X is independently selected from the group consisting of Cl, Br, I, F, $NO_3$, $NO_2$, $SO_3$ and $SO_4$, and a safe and effective amount of a topical carrier.

The present invention also relates to a method of regulating wrinkles comprising topically applying a composition comprising a benzofuran derivative having the structure

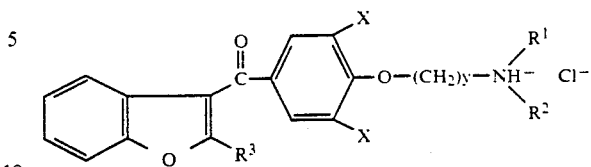

wherein $R^1$, $R^2$, $R^3$, y and X are as previously defined, and a safe and effective amount of a topical carrier.

DETAILED DESCRIPTION OF THE INVENTION

As used herein, "alkyl" means an unsubstituted carbon-containing chain which may be straight, branched or cyclic; saturated, monounsaturated (i.e., one double or triple bond in the chain), or polyunsaturated (i.e., two or more double bonds in the chain; two or more triple bonds in the chain; one or more double and one or more triple bonds in the chain).

As used herein, "topical application" means directly laying on or spreading on outer skin.

As used herein, "pharmaceutically-acceptable" means that drugs, medicaments or inert ingredients which the term describes are suitable for use in contact with the tissues of humans and lower animals without undue toxicity, incompatability, instability, irritation, allergic response, and the like, commensurate with a reasonable benefit/risk ratio.

As used herein, "anti-wrinkle agent" means a benzofuran derivative having the structure

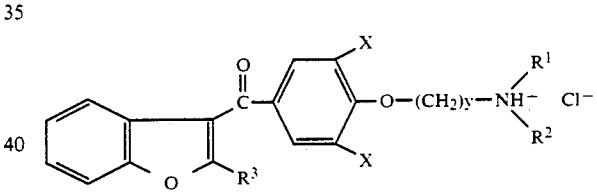

wherein $R^1$ and $R^2$ are each independently methyl or ethyl, $R^3$ is a $C_1$-$C_4$ alkyl, y is an integer from 1 to about 3 and each X is independently selected from the group consisting of Cl, Br, I, F, $NO_3$, $NO_2$, $SO_3$ and $SO_4$. Preferably the anti-wrinkle agent is amiodarone.

As used herein, "regulating wrinkles" means preventing, retarding, arresting, or reversing the process of wrinkle formation in mammalian skin.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein, all percentages are by weight unless otherwise specified.

Active Agent

The present invention relates to a composition for topical application for regulating wrinkles in mammalian skin comprising a benzofuran derivative having the structure

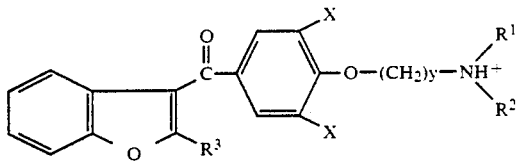

and a pharmaceutically acceptable topical carrier.

$R^1$ and $R^2$ are independently methyl or ethyl, preferably both $R^1$ and $R^2$ are ethyl.

$R^3$ is a $C_1$-$C_4$ alkyl, preferably $C_4$, preferably saturated, preferably straight chain.

y is an integer from 1 to about 3, preferably 2.

X is selected from the group consisting of I, Cl, Br, Fl, $NO_3$, $NO_2$, $SO_3$ and $SO_4$; preferably I, Cl, Br and Fl; more preferably I and Cl; most preferably I.

In a specific embodiment, the present invention relates to a composition for topical application for regulating wrinkles in mammalian skin comprising a safe and effective amount of amiodarone having the structure

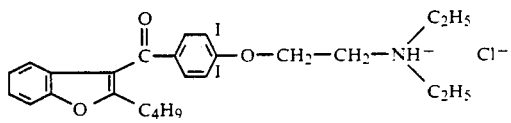

and a pharmaceutically-acceptable topical carrier.

Carriers

In addition to the active agent as previously described, the pharmaceutical compositions of the present invention comprise a pharmaceutically-acceptable carrier. The term "pharmaceutically-acceptable carrier", as used herein, means one or more compatible solid or liquid filler diluents or microencapsulating substances which are suitable for administration to a human or lower animal. Pharmaceutically-acceptable carriers must be of sufficiently high purity and sufficiently low toxicity to render them suitable for administration to the human or lower animal being treated. A safe and effective amount of carrier is from about 50% to about 90%, preferably from about 90% to about 99.99% of the composition.

Variations in formulation of these carriers will result in a wide variety of products which fall within the scope of the present invention.

Pharmaceutical Compositions

The topical pharmaceutical compositions of the present invention may be made into a wide variety of product types. These include, but are not limited to lotions, creams, beach oils, gels, sticks, sprays, ointments, pastes, mousses and cosmetics. These product types may comprise several types of carrier systems including, but not limited to, solutions, emulsions, gels and solids.

The topical pharmaceutical compositions of the present invention formulated as solutions typically include a pharmaceutically-acceptable aqueous or organic solvent. The terms "pharmaceutically-acceptable aqueous solvent" and "pharmaceutically-acceptable organic solvent" refer to a solvent which is capable of having dispersed or dissolved therein the anti-wrinkle agent, and possesses acceptable safety properties (e.g., irritation and sensitization characteristics). Water is a typical aqueous solvent. Examples of suitable organic solvents include: propylene glycol, polyethylene glycol (200-600), polypropylene glycol (425-2025), glycerol, 1,2,4-butanetriol, sorbitol esters, 1,2,6-hexanetriol, ethanol, isopropanol, butanediol, and mixtures thereof. These solutions contain from about 0.01% to about 20%, more preferably from about 0.1% to about 10% of the anti-wrinkle agent, and from about 80% to about 99.99%, more preferably from about 90% to about 99.9% of an acceptable aqueous or organic solvent.

If the topical pharmaceutical compositions of the present invention are formulated as an aerosol and applied to the skin as a spray-on, a propellant is added to a solution composition. Examples of propellants useful herein include, but are not limited to, the chlorinated, fluorinated and chloro-fluorinated lower molecular weight hydrocarbons. A more complete disclosure of propellants useful herein can be found in Sagarin, *Cosmetics Science and Technology*, 2nd Edition, Vol. 2, pp. 443-465 (1972).

Topical pharmaceutical compositions of the present invention may be formulated as a solution comprising an emollient. An example of a composition formulated in this way would be a beach oil product. Such compositions contain from about 0.01% to about 20% of the anti-wrinkle agent and from about 2% to about 50% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32-43 (1972), incorporated herein by reference, contains numerous examples of suitable materials.

A lotion can be made from a solution carrier system. Lotions typically comprise from about 0.01% to about 20%, preferably from about 0.1% to about 10%, of the anti-wrinkle agent; from about 1% to about 20%, preferably from about 5% to about 10%, of an emollient; and from about 50% to about 90%, preferably from about 60% to about 80%, water.

Another type of product that may be formulated from a solution carrier system is a cream. A cream of the present invention would comprise from about 0.01% to about 20%, preferably from about 0.1% to about 10%, of the anti-wrinkle agent; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Segarin, *Cosmetics, Science and Technology*, 2nd Edition, Vol. 1, pp. 72-73 (1972).

If the carrier is formulated as an emulsion, from about 1% to about 10%, preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's *Detergents and Emulsifiers*, North American Edition, pages 317-324 (1986); the disclosures of which are incorporated herein by reference. Preferred emulsifiers are anionic or nonionic, although the other types may also be used.

Lotions and creams can be formulated as emulsions as well as solutions. Typically such lotions comprise from about 0.01% to about 20%, preferably from about 0.1% to about 10%, of the anti-wrinkle agent; from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would typically comprise from about 0.01% to about 20%, preferably from about 0.1% to about 10%, of the anti-wrinkle agent; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

Single emulsion skin care preparations, such as lotions and creams, of the oil-in-water type and water-in-oil type are well-known in the cosmetic art and are useful in the present invention. Multiphase emulsion compositions, such as the water-in-oil-in-water type, as disclosed in U.S. Pat. No. 4,254,105, Fakuda et al., issued Mar. 3, 1981, incorporated herein by reference, are also useful in the present invention. In general, such single or multiphase emulsions contain water, emollients and emulsifiers as essential ingredients.

Triple emulsion carrier systems comprising an oil-in-water-in-silicone fluid emulsion composition as disclosed in U.S. Pat. No. 4,960,764, Figueroa, issued Oct. 2, 1990, are also useful in the present invention. This triple emulsion carrier system can be combined with from about 0.01% to about 20%, preferably from about 0.1% to about 10%, o the anti-wrinkle agent to yield the topical pharmaceutical composition of the present invention.

Another emulsion carrier system useful in the topical pharmaceutical compositions of the present invention is a microemulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with from about 0.1% to about 10% of the anti-wrinkle agent.

If the topical pharmaceutical compositions of the present invention are formulated as a gel or a cosmetic stick, a suitable amount of a thickening agent, as disclosed supra, is added to a cream or lotion formulation.

The topical pharmaceutical compositions of the present invention may also be formulated as makeup products such as foundations.

The topical pharmaceutical compositions of the present invention may contain, in addition to the aforementioned components, a wide variety of additional oil-soluble materials and/or water-soluble materials conventionally used in topical compositions, at their art-established levels.

Various water-soluble materials may also be present in the compositions of this invention. These include humectants, proteins and polypeptides, preservatives and an alkaline agent. In addition, the topical compositions herein can contain conventional cosmetic adjuvants, such as dyes, opacifiers (e.g., titanium dioxide), pigments and perfumes.

The topical pharmaceutical compositions of the present invention may also include a safe and effective amount of a penetration enhancing agent. A preferred amount of penetration enhancing agent is from about 1% to about 5% of the composition.

Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and European Patent Application 0043738, Cooper et al., published Jan. 13, 1982.

Other conventional skin care product additives may also be included in the compositions of the present invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions of the present invention. For example, Vitamin A, and derivatives thereof, Vitamin $B_2$, biotin, pantothenic, Vitamin D, and mixtures thereof may be used.

Cleaning Compositions

The skin cleaning compositions of the present invention comprise, in addition to the anti-wrinkle agent, a cosmetically-acceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with the anti-wrinkle agent in a manner such that there is no interaction which would substantially reduce the efficacy of the composition for regulating skin wrinkles.

The skin cleaning compositions of the present invention contain from about 0.01% to about 20%, preferably from about 0.1% to about 10%, of the anti-wrinkle agent and from about 1% to about 90%, preferably from about 5% to about 10%, of a cosmetically-acceptable surfactant.

The physical form of the skin cleansing compositions is not critical. The compositions can be, for example, formulated as toilet bars, liquids, pastes, or mousses. Toilet bars are most preferred since this is the form of cleansing agent most commonly used to wash the skin.

The surfactant component of the compositions of the present invention are selected from anionic, nonionic, zwitterionic, amphoteric and ampholytic surfactants, as well as mixtures of these surfactants. Such surfactants are well-known to those skilled in the detergency art.

The cleaning compositions of the present invention can optionally contain, at their art-established levels, materials which are conventionally used in skin cleansing compositions.

Combination Actives

A. Sunscreens and Sunblocks

Optimum regulation of skin wrinkling resulting from exposure to U.V. light can be obtained by using a combination of the anti-wrinkle agent of the present invention together with sunscreens or sunblocks. Useful sunblocks include, for example, zinc oxide and titanium dioxide.

Photo damage is a predominant cause of skin wrinkling. Thus, for purposes of wrinkle prevention, the combination of the anti-wrinkle agent with a UVA and/or UVB sunscreen would be most desirable. The inclusion of sunscreens in compositions of the present invention at low levels will not significantly reduce the tanning response of the user but will enhance immediate protection against acute UV damage.

A wide variety of conventional sunscreening agents are suitable for use in combination with the anti-wrinkle agent. Segarin, et al., at Chapter VIII, pages 189 et seq., of *Cosmetics Science and Technology*, disclose numerous suitable agents. Specific suitable sunscreening agents include, for example: p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropyleneglycol esters); Cinnamic acid derivatives (menthyl and benzyl esters, α-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbotol) (6-propyl piperonyl) ether; Hydroquinone; Benzophenones (Oxybenzene, Sulisobenzone, Dioxybenzone, Benzoresorcinol, 2,2′,4,4′-Tetrahydroxybenzophenone, 2,2′-Dihydroxy-4,4′-dimethoxybenzophenone, Octabenzone; 4-Isopropyldibenzoylmethane; Butylmethoxydibenzomethane; Etocrylene; and 4-isopropyl-di-benzoylmethane.

Of these, 2-ethylhexyl-p-methoxycinnamate, 4,4′-t-butylmethoxydibenzoylmethane, 2-hydroxy-4-methoxybenzophenone, octyldimethyl-p-aminobenzoic acid, digalloyltrioleate, 2,2-dihydroxy-4-methoxybenzophenone, ethyl-4-[bis(hydroxypropyl)]aminobenzoate, 2-ethylhexyl-2-cyano-3,3-diphenylacrylate, 2-ethylhexyl-salicylate, glyceryl-p-aminobenzoate, 3,3,5-trimethyl-cyclohexylsalicylate, methylanthranilate, p-dimethyl-aminobenzoic acid or aminobenzoate, 2-ethylhexyl-p-dimethylamino-benzoate, 2-phenylbenzimidazole-5-sulfonic acid, 2-(p-dimethylaminophenyl)-5-sulfonicbenzoazoic acid and mixtures of these compounds, are particularly useful.

Preferred sunscreens useful in the compositions of the present invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

A safe and effective amount of sunscreen may be used in the anti-wrinkle agent compositions of the present invention. The sunscreening agent must be compatible with the anti-wrinkle agent. Generally the composition may comprise from about 1% to about 20%, preferably from about 2% to about 10%, of a sunscreening agent. Exact amounts will vary depending upon the sunscreen chosen and the desired Sun Protection Factor (SPF).

Also particularly useful in the present invention are sunscreens such as those disclosed in Sabatelli, U.S. patent application Ser. No. 054,085 (filed Jun. 2, 1987) and Sabatelli et al., U.S. patent application Ser. No. 054,046 (filed Jun. 2, 1987). The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-di-hydroxybenzophenone; N,N-di-(2-ethylhexyl)-4-aminobenzoic acid ester with 4-hydroxydibenzoylmethane; 4-N,N-(2-ethylhexyl)methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl)-methylaminobenzoic acid ester of 4-(2-hydroxyethoxy)dibenzoylmethane and N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2hydroxyethoxy)dibenzoylmethane and mixtures thereof.

An agent may also be added to any of the compositions of the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred wrinkle regulating composition of the present invention, an anti-inflammatory agent is included as an active along with the anti-wrinkle agent. The inclusion of an anti-inflammatory agent enhances the wrinkling regulating benefits of the compositions. The anti-inflammatory agent protects strongly in the UVA radiation range (though it also provides some UVB protection as well) thereby preventing further wrinkle formation caused by UV radiation, while the anti-wrinkle agent regulates existing wrinkles. Thus the combination provides broad protection. The topical use of anti-inflammatory agents reduces photoaging of the skin resulting from chronic exposure to UV radiation. (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions of the present invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use in the present invention is hydrocortisone.

A second class of anti-inflammatory agents which is useful in the compositions of the present invention includes the nonsteroidal anti-inflammatory agents. The variety of compounds encompassed by this group are well-known to those skilled in the art. For detailed disclosure of the chemical structure, synthesis, side effects., etc., of non-steroidal anti-inflammatory agents, reference may be had to standard texts, including *Anti-inflammatory and Anti-Rheumatic Drugs*, K. D. Rainsford, Vol. I-III, CRC Press, Boca Raton, (1985), and *Anti-inflammatory Agents, Chemistry and Pharmacology*. 1, R. A. Scherrer, et al., Academic Press, New York (1974).

Specific non-steroidal anti-inflammatory agents useful in the composition of the present invention include, but are not limited to:
1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and
6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the present invention are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di- tert-butyl phenol derivatives. For example, compounds selected from 4-(4',-pentyn-3'one)-2,6-di-t-butylphenol; 4-(5'-hexynoyl)2,6 -di-t-butylphenol; 4-((S)-(−)-3'-methyl-5'-hexynoyl)-2,6-di-t-butylphenol; 4-((R)-(+)-3'-methyl-5'-hexynoyl)-2,6-di-t-butylphenol; and 4-(3',3',-dimethoxypropionyl)-2,6-di-t-butylphenol are useful in the present invention.

Yet another class of anti-inflammatory agents which are useful in the present invention are those disclosed in U.S. Pat. No. 4,912,248, Mueller, issued Mar. 27, 1990. This patent discloses compounds and diastereomeric mixtures of specific 2-naphthyl- containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen- (R)-2-butyl ester, and diasteromeric mixtures of (S)-naproxol- (R)-2-methyl butyrate and (S)-naproxol-(S)-2-methyl butyrate are useful in the present invention.

Finally, so-called "natural" anti-inflammatory agents are useful in the present invention. For example, candelilla wax, alpha bisabolol, aloe vera, Manjistha (extracted from plants in the genus Rubia, particularly *Rubia cordifolia*), and Guggal (extracted from plants in the genus Commiohora, particularly *Commiphora mukul*), may be used.

Another preferred composition of the present invention comprises an anti-wrinkle agent, a sunscreen, and an anti-inflammatory agent together for wrinkle regulation in the amounts disclosed for each individually hereinabove.

C. Anti-Oxidants/Radical Scavengers

In a preferred wrinkle regulating composition of the present invention, an anti-oxidant/radical scavenger is included as an active along with the anti-wrinkle agent. The inclusion of an anti-oxidant/radical scavenger increases the wrinkle regulating benefits of the composition.

A safe and effective amount of an anti-oxidant/radical scavenger may be added to the compositions of the present invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy- 2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, amino-guanidine), sulfhydryl compounds (e.g., glutathione), and dihydroxy fumaric acid and its salts may be used.

In a preferred wrinkle regulating composition of the present invention, compositions comprise one, any two, or all three of a sunscreening agent, anti-inflammatory agent, and/or an anti-oxidant/radical scavenging agent included as actives along with the anti-wrinkle agent. The inclusion of two or all three of these agents with the anti-wrinkle agent increases the wrinkle effacing benefits of the composition.

D. Chelators

In a preferred wrinkle regulating composition of the present invention, a chelating agent is included as an active along with the anti-wrinkle agent. As used herein, "chelating agent" means an active agent capable of removing a metal ion from a system by forming a complex so that the metal ion cannot readily participate in or catalyze chemical reactions. The inclusion of a chelating agent increases the wrinkle regulating benefits of the composition.

A safe and effective amount of a chelating agent may be added to the compositions of the present invention, preferably from about 0.1% to about 10%, more preferably from about 1% to about 5%, of the composition. Chelators useful in compositions of the present invention are disclosed in U.S. patent application Ser. No. 251,910, Bissett, Bush & Chatterjee, filed Oct. 4, 1988, incorporated herein by reference. Preferred chelators useful in compositions of the present invention are furildioxime and derivatives thereof, more preferably amphi-2-furildioxime.

In a preferred wrinkle regulating composition of the present invention, compositions comprise one, any two, any three, or all four of a sunscreening agent, anti-inflammatory agent, anti-oxidant/radical scavenging agent, and/or chelating agent included as actives along with the anti-wrinkle agent. The inclusion of two, three, or all four of these agents with the anti-wrinkle agent increases the wrinkle regulating benefits of the composition.

E. Retinoids

In a preferred wrinkle regulating composition of the present invention, a retinoid, preferably retinoic acid, is included as an active along with the anti-wrinkle agent. The inclusion of a retinoid increases the wrinkle regulating benefits of the composition. A safe and effective amount of a retinoid may be added to the compositions of the present invention, preferably from about 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

In a preferred wrinkle regulating composition of the present invention, compositions comprise one, any two, any three, any four, and/or all five of a sunscreening agent, anti-inflammatory agent, anti-oxidant/radical scavenging agent, chelating agent, and/or a retinoid included as actives along with the anti-wrinkle agent. The inclusion of two, three, four, or all five of these agents with the anti-wrinkle agent increases the wrinkle regulating benefits of the composition.

Methods for Regulating Wrinkles in Mammalian Skin

The present invention further relates to a method for regulating wrinkles in mammalian skin. Such a method comprises topical application of a safe and effective amount of the anti-wrinkle agent. The amount of anti-wrinkle agent and frequency of application will vary widely depending upon the level of wrinkling already in existence in the subject, the rate of further wrinkle formation, and the level of regulation desired.

A safe and effective amount of anti-wrinkle agent in a topical composition is applied, generally from about 0.001 mg to about 2 mg per $cm^2$ skin per application, preferably from about 0.01 mg to about 1 mg per $cm^2$ skin per application. Application preferably ranges from about monthly to about 5 times daily, more preferably from about biweekly to about daily, more preferably still from about weekly to about 3 times per week.

A preferred method of the present invention for regulating wrinkles in mammalian skin involves applying both a safe and effective amount of the anti-wrinkle agent and a safe and effective amount of one or more of a sunscreening agent, an anti-inflammatory agent, an anti-oxidant/radical scavenging agent, a chelating agent and/or a retinoid to the skin simultaneously. As used herein, "simultaneous application" or "simultaneously" means applying the agents to the skin at the same situs on the body at about the same time. Though this can be accomplished by applying the agents separately to the skin, preferably a composition comprising all the desired agents commingled is applied to the skin. The amount of sunscreening agent applied is generally from about 0.05 mg to about 0.5 mg per $cm^2$ skin. The amount of anti-inflammatory agent applied is generally from about 0.005 mg to about 0.5 mg, preferably from about 0.01 mg to about 0.1 mg per $cm^2$ skin. The amount of anti-oxidant/radical scavenging agent generally applied is from about 0.01 mg to about 1.0 mg, preferably from about 0.05 mg to about 0.5 mg per $cm^2$ skin. The amount of chelating agent generally applied is from about 0.001 mg to about 1.0 mg, preferably from about 0.01 mg to about 0.5 mg, more preferably from about 0.05 mg to about 0.1 mg per $cm^2$ skin. The amount of retinoid applied is generally from about 0.001 mg to about 0.5 mg per $cm^2$ preferably from about 0.005 mg to about 0.1 mg per $cm^2$ skin. The amount of anti-wrinkle agent applied is generally from about 0.001 mg to about 2 mg per $cm^2$ skin per application, preferably from about 0.01 mg to about 1 mg per $cm^2$ skin per application.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE I

A simple topical composition is prepared by combining the following components utilizing conventional mixing techniques.

| Component | Percent by Weight Of Composition |
|---|---|
| Acetone | 99.87 |
| Amiodarone | 0.13 |

This composition is useful for topical application to regulate skin wrinkles. Use of an amount of the composition to deposit about 0.01 mg/cm² of the anti-wrinkle agent to the skin is appropriate.

EXAMPLE II

A cationic oil-in-water emulsion is prepared by combining the following components utilizing conventional mixing techniques.

| Component | Percent by Weight Of Composition |
|---|---|
| Deionized Water | 85.05 |
| Butylene Glycol | 2.00 |
| Methyl Paraben | .20 |
| Distearyl Dimethyl Ammonium Chloride | 2.00 |
| Octyl Methoxycinnamate | 7.50 |
| Amiodarone | .10 |
| Cetyl Alcohol | 1.50 |
| Stearyl Alcohol | 1.50 |
| Propyl Paraben | .15 |

This composition is useful for topical application to regulate skin wrinkles. Use of an amount of the composition sufficient to deposit about 0.01 mg/cm² of the anti-wrinkle agent to the skin is appropriate.

EXAMPLE III

An ion pair oil-in-water emulsion is prepared by combining the following components utilizing conventional mixing techniques.

| Component | Percent by Weight Of Composition |
|---|---|
| Deionized Water | 78.95 |
| Permulon TR-2 (C10-C30 Acrylate Copolymer. B. F. Goodrich | .30 |
| Distearyl Dimethyl Ammonium Chloride | .15 |
| Amiodarone | .10 |
| 4-N,N-(2-ethylhexyl)methylaminobenzoic acid 4-ester of 2-hydroxy-4-(2-hydroxyethoxy)-benzophenone ("Compound 6") | 4.00 |
| 4-N,N-(2-ethylhexyl)methylaminobenzoic acid ester of 4-(2-hydroxyethoxy) dibenzoylmethane | 2.00 |
| Dimethyl Isosorbide | 6.00 |
| Dioctyl Malate | 6.00 |
| Cetyl Alcohol | 1.00 |
| Stearyl Alcohol | 1.00 |
| 99% Triethanolamine | .50 |

This composition is useful for topical application to regulate skin wrinkles. Use of an amount of the composition sufficient to deposit about 0.01 mg/cm² of anti-wrinkle agent to the skin is appropriate.

EXAMPLE IV

A sunscreen composition is prepared by combining the following components utilizing conventional mixing techniques.

| Component | Percent by Weight of Composition |
|---|---|
| Polypropylene Glycol 15 Stearyl Ether | 15.00 |
| Sorbitan Oleate | 2.00 |
| Octyl Methoxy Cinnamate | 7.50 |
| Amiodarone | .10 |
| Propyl Paraben | .15 |
| Butylated Hydroxy Toluene | .05 |
| Cyclomethicone | 20.00 |
| Sesame Oil | 5.00 |
| Mineral Oil (Blandol) | 50.20 |

This composition is useful for topical application to regulate skin wrinkles. Use of an amount of the composition is sufficient to deposit about 0.01 mg/cm² antiwrinkle agent to the skin is appropriate.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A method of regulating wrinkles in mammalian skin comprising topically applying a composition comprising:

a) from about 0.01% to about 20% of a benzofuran derivative having the structure

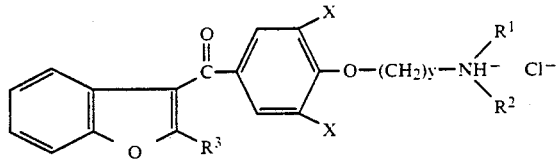

wherein $R^1$ and $R^2$ are each independently methyl or ethyl; $R^3$ is a $C_1$-$C_4$ alkyl; y is an integer from 1 to about 3; and each X is independently selected form the group consisting of Cl, Br, I, F, $NO_3$, $NO_2$, $SO_3$ and $SO_4$; and b) a safe and effective amount of a topical carrier comprising from about 1% to about 50% of an emollient such that from about 0.001 mg to about 2 mg of the benzofuran derivative is applied per cm² of skin.

2. The method of claim 1 wherein the composition comprises from about 0.01% to about 10% of the benzofuran derivative.

3. The method of claim 2 wherein $R^1$ and $R^2$ are both ethyl.

4. The method of claim 3 wherein $R^3$ is n-butyl.

5. The method of claim 4 wherein X is independently selected for the group consisting of Cl and I.

6. The method of claim 5 wherein y is 2.

7. The method of claim 2 wherein the benzofuran derivative is amiodarone.

8. The method of claim 1 wherein the composition also comprises from about 1% to about 20% of a sunscreen agent.

9. The method of claim 7 wherein the composition also comprises from about 1% to about 20% of a sunscreen agent.

10. The method of claim 1 wherein the composition also comprises from about 0.01% to abut 10% of an anti-inflammatory agent.

11. The method of claim 1 wherein the composition also comprises from about 0.1% to about 10% of a chelating agent.

* * * * *

UNITED STATES PATENT AND TRADEMARK OFFICE
CERTIFICATE OF CORRECTION

PATENT NO. : 5,118,707

DATED : June 2, 1992

INVENTOR(S) : R. Chatterjee and R. Kapoor

It is certified that error appears in the above-identified patent and that said Letters Patent is hereby corrected as shown below:

Column 14, line 64, "abut" should read --about--.

In the Abstract, in the structure, "$NH^-$" should read --$NH^+$--.

Column 1, line 34, "5 6" should read --5.6--.

Column 1, line 57, "$NH^-$" should read --$NH^+$--.

Column 2, line 6, "$NH^-$" should read --$NH^+$--.

Column 2, line 39, "$NH^-$" should read --$NH^+$--.

Column 2, line 46, "$SO_3$and" should read --$SO_3$ and--.

Column 3, line 11, "$NH^-$" should read --$NH^+$--.

Column 3, line 31, "$NH^-$" should read --$NH^+$--.

Column 5, line 62, "supra" should read --_supra_--.

Column 7, lines 61 and 62, "2.2-dihydroxy-4 -methoxybenzophenone" should read --2,2-dihydroxy-4-methoxybenzophenone--.

Columns 7 and 8, lines 68 and 1, respectively, "sulfonicbenzoazoic" should read --sulfonicbenzoxazoic--.

Column 8, line 36, "dibenzoylmethane" should read --dibenzoylmethane;--.

Column 8, line 65, "chronic" should read --_chronic_--.

Column 10, line 20, "-t-" should read -- -_t_- --.

Column 10, line 20, "-t-" should read -- -_t_- --.

Column 10, line 21, "-t-" should read -- -_t_- --.

Column 10, line 23, "-t-" should read -- -_t_- --.

Column 10, line 24, "-t-" should read -- -_t_- --.

Column 12, line 52, "$cm^2$ preferably" should read --$cm^2$ skin, preferably--.

Column 14, line 31, "$NH^-$" should read --$NH^+$--.

UNITED STATES PATENT AND TRADEMARK OFFICE
CERTIFICATE OF CORRECTION

PATENT NO. : 5,118,707

DATED : June 2, 1992

INVENTOR(S) : R. Chatterjee and R. Kapoor

It is certified that error appears in the above-identified patent and that said Letters Patent is hereby corrected as shown below:

Column 14, line 49, "0.01%" should read --0.1%--.

Column 14, line 64, "0.01%" should read --0.1%--.

Signed and Sealed this

Ninth Day of November, 1993

BRUCE LEHMAN

*Attest:*

*Attesting Officer*  *Commissioner of Patents and Trademarks*